United States Patent [19]

Bustos

[11] Patent Number: 4,840,629

[45] Date of Patent: Jun. 20, 1989

[54] MAMMARY PROSTHESIS

[75] Inventor: Ricardo A. Bustos, Sao Paulo, Brazil

[73] Assignee: Silimed Silicone E Instrumental Medico-Cirurgico e Hospitalar Ltda., Rio de Janeiro, Brazil

[21] Appl. No.: 255,278

[22] Filed: Oct. 11, 1988

[30] Foreign Application Priority Data

Oct. 14, 1987 [BR] Brazil ................................ PI8705600

[51] Int. Cl.⁴ .............................................. A61F 2/12
[52] U.S. Cl. ........................................ 623/8; 128/898; 623/11
[58] Field of Search ........................... 623/8, 7, 11, 15; 128/334 R, 898; 450/55–57

[56] References Cited

U.S. PATENT DOCUMENTS

| | | | |
|---|---|---|---|
| 2,671,444 | 3/1954 | Pease | 128/334 R |
| 2,959,173 | 11/1960 | Douthit | 623/7 X |
| 4,372,293 | 2/1983 | Vijil-Rosales | 623/7 X |
| 4,769,036 | 9/1988 | Modir | 623/8 |
| 4,778,465 | 10/1988 | Wilkins | 623/8 |

Primary Examiner—Ronald L. Frinks
Attorney, Agent, or Firm—Morgan & Finnegan

[57] ABSTRACT

A "MAMMARY PROSTHESIS", including a perforated lamina (10) made of an inert and flexible material, having a thickness not exceeding 1.0 mm and showing, when flattened, the approximate shape of an annular sector, with an extension of about 180° to about 220°, the inner diameter and the flexibility of the lamina in annular sector being sized in order to allow that, with the insertion of the prosthesis between the mammary gland and the datached skin, the lamina (10) will assume a substantially frustoconical shape having a slightly convex side surface and with the inner peripheral edge surrounding the mammary areola at a certain distance, the ends of the inner peripheral edge of the lamina (10) being close to each other, in such a way to occupy one of the positions adjoining and overlapping one another and the extreme edges of the lamina remaining angularly spaced apart.

8 Claims, 3 Drawing Sheets

MAMMARY PROSTHESIS

The present application refers to a mammary prosthesis particularly to a mammary prosthesis used in the reduction mammoplasty technique.

Several reduction mammoplasty techniques are known at present, the first of them being defined by an inverted "T"-shaped incision, which is made on the base of the breast and follows the direction of the mammary areola and then surrounds the latter.

In another type of reduction mammoplasty technique, the incision is "L"-shaped, and is made from the most extreme outer point of the base of the breast to the median point of it, going in the direction of the mammary areola and surrounding the latter.

In a more improved technique, such incision has been reduced to a vertical line perpendicular to the base of the breast, going in the direction of the areola and surrounding it.

In spite of the fact that the abovementioned techniques have resulted in durable and beautiful shaped breasts, and even though sectioning of the galoctophore ducts is avoided so as not to alter breast feeding capability, the cicatrices due to the incision are still substantially visible.

From long studies, it was ascertained that it would be possible to obtain a cut (slice) that would be exclusively glandular, arterialized, of lower pedicle and with no anatomical objections, by means of only one periareolar incision.

In the cases of discrete deformities, where, in the mammoplasty technique, the "W"-shaped excision of the glands was not necessary, the technique of the unique periareolar incision consists only of the division of the upper poll of such glands, into three parts, in order to facilitate the mounting of the new mammary cone.

However, it has not been found so far any means to solve the problem relating to the fitting of the breast formation cone with the detached skin regarding the support of such cone in a correct position, as the detached skin has not got any intrinsic characteristic or function of support.

It is an object of the present invention to provide a mammary prosthesis, which adapts and integrates the detached skin to the new mammary cone obtained during the reduction mammoplasty surgery.

It is another object of the present invention to provide a mammary prosthesis which helps to support the mammary cone in a correct position, and, consequently, prolongs the plastic result of the new shape obtained from the plastic surgery of the mamma.

These and other objects and advantages of the present invention will be obtained through the provision of a mammary prosthesis, which is inserted in the breast of a patient through an incision, such prosthesis comprising a perforated lamina of inert and flexible material, and a thickness not exceeding 1.0 mm and showing, when flattened, the approximate shape of an annular sector, having an extension of about 180 to about 220°, the inner diameter and the flexibility of the lamina in the annular sector being sized in such a way to allow the lamina to assume a frustoconical shape having a slightly convex side surface and the inner peripheral edges surrounding the mammary areola at a certain distance, on inserting the prosthesis between the mammary gland and the detached skin. The ends of the inner peripheral edges of the lamina are close to each other, in such a way as to occupy one of the positions adjoining and overlapping one another, and the extreme edges of the lamina remain angularly spaced apart at the rest of its extension.

In a preferred embodiment of the invention, the lamina comprises, at its extreme edges, a pair of inner peripheral projections having a tapered shape, and an angular extension of around 45° each, and a pair of outer peripheral projections having an angular extension of about 30° each, when both inner peripheral projections are arranged in the mammary cone, they overlap one another in at least part of its extension.

By the above mentioned prosthesis, it is achieved simultaneously a means of support for the mammary cone and a high degree of integration between the detached skin and the gland, due to the development of the fibrous reaction through the lamina perforation, and the provision of the outer peripheral projections allows the prosthesis to be sutured directly to the pectoral musculature of the patient, increasing its capacity of supporting the mammary cone.

The overlapping of the inner peripheral projections renders a better fixation and retention of the conical shape to be imparted to the lamina while the gap between the extreme edges or the outer peripheral projections avoids constriction of the tissue, when there are increases in the glandular volume.

The invention will be better understood when taken in conjunction with the annexed drawings, wherein.

Figure 1:
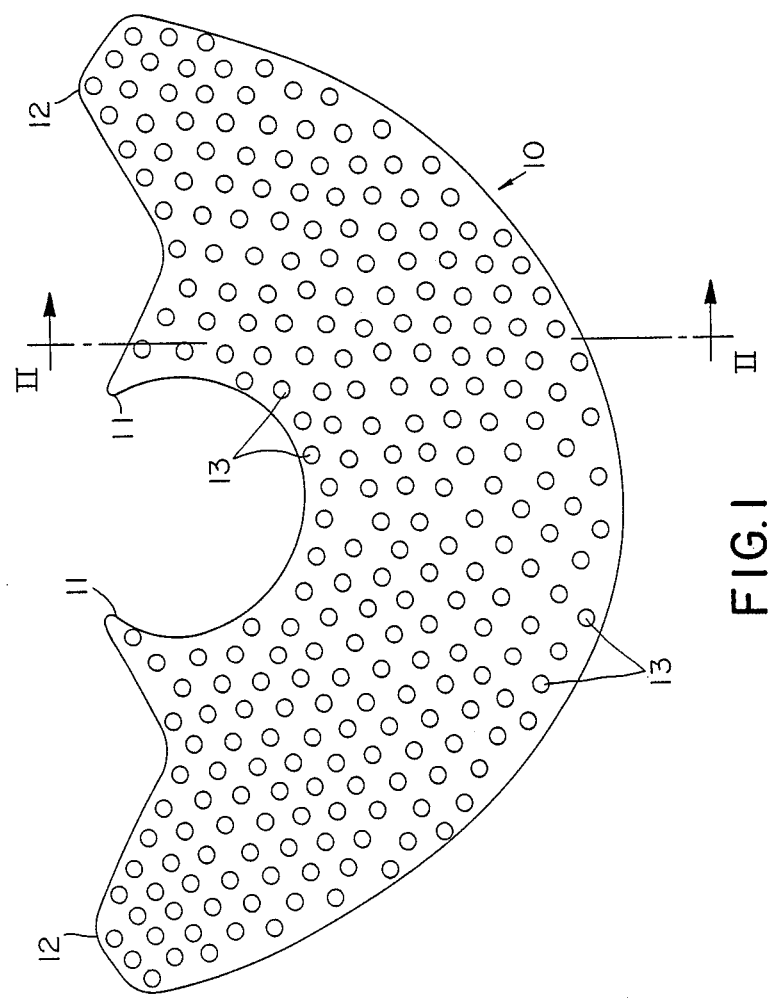
FIG. 1 is a frontal view of the flattened mammary prosthesis.
Figure 2:
FIG. 2 is a sectional view taken according to line II—II in FIG. 1.
Figure 3:
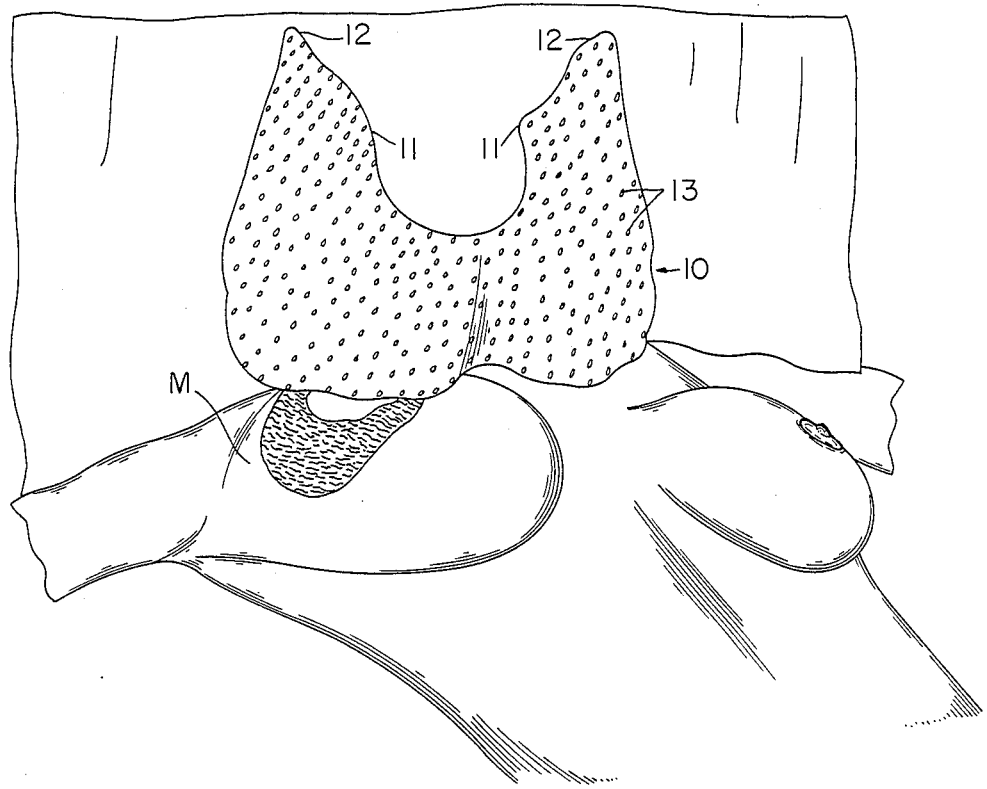
FIG. 3 shows the breast of a patient ready to receive the mammary prosthesis in question.
Figure 4:
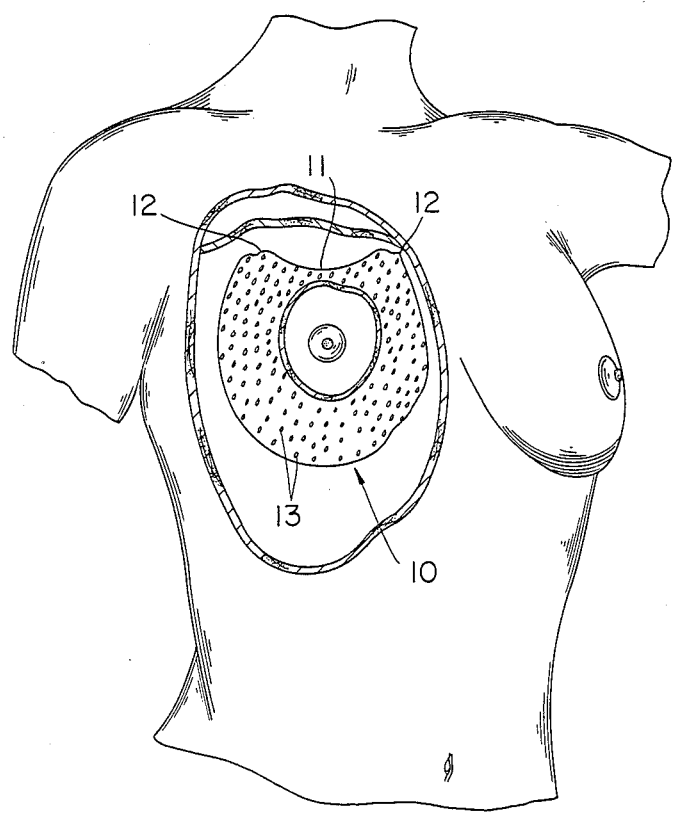
FIG. 4 shows the mammary prosthesis in question adapted over the gland, in a W-shape, after setting up the mammary cone.

According to such illustrations, the mammary prosthesis in question is defined by a silicone-made lamina 10, having a thickness of preferably about 0.005 mm, and with an approximate shape of an annular sector, when flattened, and an angular extension of about 180° to about 200°.

Subsequent to the periareolar incision and the removal of the mammary areola and mounting of the new mammary cone, the lamina 10 is inserted between the gland and the detached skin, covering part of the mammary cone and the entire peripheral region of the mammary areola.

Such covering of the peripheral region of the mammary areola is achieved by the provision of a pair of inner projections 11 having about 45° each, and incorporated into the lamina 10, symmetrical to the axial axis of the annular sector and concordant with the inner circular peripheral edge of the lamina. The inner projections 11 end in a point in order to facilitate their overlapping, to form a circular collar around the mammary areola of the patient, such projections being kept spaced apart from the areola at a distance of about 3 mm, so that they do not interfere with the cicatricial process of the region that is to be sutured.

The lamina 10 further comprises a pair of outer peripheral projections 12 having an extension of about 30° each, symmetrical to the axial axis of the annular sector and concordant with the outer peripheral edge of the lamina, such projections being sutured to the pectoral muscles of the patient in order to assure their positioning and to increase their capacity of support. The outer peripheral projections 12 partially cover the mammary cone, angularly spaced apart in order to avoid constriction of the tissue when there is an increase in volume caused, for instance, by menstruation and pregnancy.

The lamina 10 comprises a plurality of circular holes 13 preferably arranged in concentric alignment with the lamina in the circular sector 10, occupying the entire area of the latter, and allowing the total integration of the prosthesis with the gland and the detached skin, and thus stimulating the fibrous reaction process through the lacing and passing through the lamina/gland/detached skin combination.

Such fibrous reactive process contributes to an important retractive effect over the skin due to the organic reaction to the silicone material, and is fundamental to the aesthetic result of the new mammoplasty technique as the cutaneous retraction not only means accommodation of the skin over the new mammary cone, but, mainly, an adaptation made therebetween.

Finally, it should be noted that the mammary prosthesis, object of the present invention, can be applied not only in periareolar incisions, but also in other incisions such as, for example, the vertical line type, inasmuch as in the case of high or grave hypertrophies or substantial ptoses, there will fatally be an excess of exaggerated skin, and the cutaneous retraction caused by the fibrous reaction will not be sufficient for an harmonious adaptation. Therefore, in this case, it is indispensable the excision of such excess of skin and, consequently, the vertical cicatricial sequela will be inevitable.

I claim:

1. MAMMARY PROSTHESIS, to be inserted in the breast of a patient by an incision, characterized by comprising a perforated lamina (10) made of an inert and flexible material, having a thickness not exceeding 1.0 mm and showing, when flattened, the approximate shape of an annular sector, with an extension of about 180° to about 220°, the inner diameter and the flexibility of the lamina in the annular sector being sized in order to allow the lamina (10) to assume a substantially frustoconical shape having a slightly convex side surface and the inner peripheral edge surrounding the mammary areola at a certain distance, on inserting the prosthesis between the mammary gland and the detached skin, the ends of the inner peripheral edge of the lamina (10) being close to each other in such a way to occupy one of the positions adjoining and overlapping one another and the extreme edges of the lamina remaining angularly spaced apart.

2. MAMMARY PROSTHESIS, according to claim 1, characterized in that the extreme edges of the lamina (10) show inner peripheral projections (11) having an angular extension of about 45° each.

3. MAMMARY PROSTHESIS, according to claim 2, characterized in that said inner projections (11) are symmetrical to the axial axis of the annular sector and concordant with the inner circular peripheral edge of the lamina (10).

4. MAMMARY PROSTHESIS, according to claim 2, characterized in that said inner peripheral projections (11) show a tapered shape and are at least partially overlapping one another when the prosthesis is applied.

5. MAMMARY PROSTHESIS, according to claim 1, characterized in that the inner peripheral edge is spaced apart about 3 mm from the mammary areola when inserted in the breast.

6. MAMMARY PROSTHESIS, according to claim 1, characterized in that end edges of lamina (10) show outer peripheral projections (12) having an angular extension of about 30° each.

7. MAMMARY PROSTHESIS, according to claim 6, characterized in that outer peripheral projections (12) are symmetrical to the axial axis of the annular sector and concordant with the outer peripheral edge of the lamina (10).

8. MAMMARY PROSTHESIS, according to claim 1, characterized in that the opposed and outer extreme portions (12) of lamina (10) are adapted to be fixed to the pectoral musculature of the patient.

* * * * *